(12) United States Patent
Ding

(10) Patent No.: US 7,022,334 B1
(45) Date of Patent: Apr. 4, 2006

(54) THERAPEUTIC COMPOSITION AND A METHOD OF COATING IMPLANTABLE MEDICAL DEVICES

(75) Inventor: Ni Ding, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 661 days.

(21) Appl. No.: 10/104,179

(22) Filed: Mar. 20, 2002

(51) Int. Cl.
    *A61F 2/02* (2006.01)

(52) U.S. Cl. .................... 424/423; 424/424; 424/425
(58) Field of Classification Search ................ 424/423, 424/424, 425
    See application file for complete search history.

(56) References Cited

U.S. PATENT DOCUMENTS

| | | | |
|---|---|---|---|
| 4,977,901 A | 12/1990 | Ofstead | 128/772 |
| 5,112,457 A | 5/1992 | Marchant | 204/165 |
| 5,328,471 A | 7/1994 | Slepian | 604/101 |
| 5,455,040 A | 10/1995 | Marchant | 424/426 |
| 5,464,650 A | 11/1995 | Berg et al. | 427/2.3 |
| 5,578,073 A | 11/1996 | Haimovich et al. | 623/1 |
| 5,605,696 A | 2/1997 | Eury et al. | 424/423 |
| 5,620,738 A * | 4/1997 | Fan et al. | 427/2.3 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,873,904 A | 2/1999 | Ragheb et al. | 623/1 |
| 5,879,697 A | 3/1999 | Ding et al. | 424/422 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,015,541 A | 1/2000 | Greff et al. | 424/1.25 |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

* cited by examiner

*Primary Examiner*—Carlos A. Azpuru
(74) *Attorney, Agent, or Firm*—Squire, Sanders & Dempsey

(57) ABSTRACT

A therapeutic composition is provided including a polysaccharide or a cationic peptide dissolved in an organic substance. The polysaccharide can be heparin or a derivative of heparin. The cationic peptide can be L-arginine, oligo-L-arginine or poly-L-arginine. The organic substance can be formamide. A method of coating an implantable medical device is also provided, comprising applying the therapeutic composition to the device and allowing the organic substance to evaporate. The device can be a stent.

61 Claims, 2 Drawing Sheets

THERAPEUTIC COMPOSITION AND A METHOD OF COATING IMPLANTABLE MEDICAL DEVICES

BACKGROUND OF THE INVENTION

1. Field of the Invention

This invention relates to compositions such as those used for coating implantable medical devices such as stents.

2. Description of Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis may develop shortly after the procedure and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small lumens via catheters, and then expanded to a larger diameter once they are at the desired location. Biological therapy for reducing or eliminating thrombosis or restenosis can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

Local delivery can be accomplished by coating the stent with a polymeric carrier containing a biologically active agent. A polymer dissolved in an organic solvent and the agent added thereto are applied to the stent and the organic solvent is allowed to evaporate, leaving a polymeric coating impregnated with the agent.

Biologically active agents including polysaccharides, e.g., heparin, and polycationic peptides, e.g., poly-L-arginine have proven to provide beneficial effects in the treatment of thrombosis and restenosis, more particularly when used in conjunction with a stent. However, incorporation of these compounds into a polymeric carrier has proven to be challenging due to such compounds' limited solubility. To pose the problem more concretely by way of example, heparin is soluble in water but not in organic solvents, while conventional polymers used for the sustained release of heparin are soluble in organic solvents but not water. To avoid the problem of solubility incompatibility, efforts have been made to fabricate heparin-polymer coatings from heparin-polymer suspensions. For example, U.S. Pat. Nos. 5,837,313 and 5,879,697, disclose micronizing heparin followed by physically blending with a polymer and solvent to form the suspension. The suspension methods have drawbacks and disadvantages. The manufacturing process, for example, requires spraying equipment capable of handling particles. In addition, heparin-polymer suspensions lack sufficient stability in the absence of suspension agents and require constant agitation during the coating process.

Alternatively, a complex of heparin with a cationic surfactant can be formed for converting the heparin into an organically soluble compound. Examples of suitable surfactant counter ions include benzalkonium and tridodecylmethyl ammonium. However, a surfactant-bound heparin has lower antithrombotic activity because the surfactant alters heparin's charge balance and binding coefficient with coagulation cofactors.

In view of the foregoing, there is a need to prepare a true solution of polysaccharides and cationic peptides with organic solvent compositions commonly used to form polymeric coatings on implantable medical devices.

SUMMARY

In accordance with one embodiment of the invention, a therapeutic composition comprising a polysaccharide or a cationic peptide dissolved in an organic substance is provided. The polysaccharide can be heparin, heparin salts, heparinoids, heparin-based compounds, heparin having a hydrophobic counter-ion, dermatan sulfate, keratan sulfate, chondroitin sulfate, hyaluronic acid and hyaluronates. The cationic peptide can be L-arginine, oligo-L-arginine, poly-L-arginine, or arginine-containing peptide. The organic substance can be formamide.

In accordance with another embodiment of the invention, a method of coating an implantable medical device, for example a stent, is provided, comprising applying the above mentioned composition to the device and allowing the organic substance to evaporate.

In accordance with another embodiment, a method of coating a stent is provided. The method includes the acts of preparing a solution comprising heparin or a heparin derivative in an organic substance; applying the solution to the stent; and allowing the organic substance to evaporate. The organic substance can be formamide. In one embodiment, the method additionally includes combining the solution with a composition including a polymer and optionally a biologically active substance. The polymer can be, for example, poly(ethylene-co-vinyl alcohol), polyacrylates, poly(ethylene glycol), polyurethanes, polyesters, fluorinated polymers, and mixtures or combinations thereof. The biologically active substance can be, for example, actinomycin D, rapamycin, taxol, estradiol, poly(ethylene glycol)/poly (ethylene oxide), and derivatives thereof.

In accordance with another embodiment, a method for coating a stent is provided, comprising preparing a solution comprising L-arginine, or polymers or oligomers thereof, in an organic substance; applying the solution to the stent, and allowing the organic substance to evaporate. The organic substance can be formamide. In one embodiment, the method additionally comprises combining the solution with a composition including a polymer and optionally a biologically active substance.

DETAILED DESCRIPTION

Figure 1:
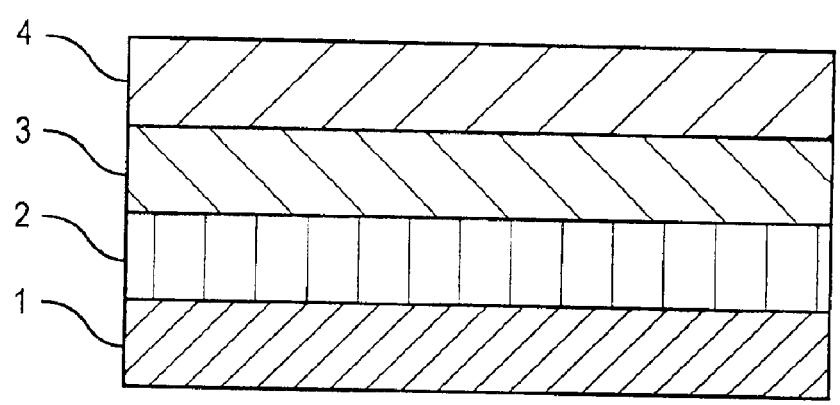
FIG. 1 schematically depicts a cross-section of a coating on a stent in accordance with one embodiment of the present invention.

FIG. 1 illustrates a partial cross section of a substrate 1 of an implantable medical device, such as a stent, having a coating. The coating can include, for example, an optional primer layer 2, a reservoir layer 3, and an optional topcoat layer 4. According to one embodiment of the present invention, the reservoir layer 3 can comprise a polymer and a polysaccharide. One example of a biologically active polysaccharide is heparin or a heparin derivative. Heparin is known to have an antithrombotic property, among other biologically active functions, and can be made from a mixture of sulfated polysaccharide chains based on D-glucosamine and D-glucoronic or L-iduronic acid.

"Heparin derivative" or "derivative of heparin" is intended to include any functional or structural variation of heparin. Representative variations include alkali metal or alkaline-earth metal salts of heparin, such as sodium heparin (also known as hepsal or pularin), potassium heparin (formerly known as clarin), lithium heparin, calcium heparin (also known as calciparine), magnesium heparin (also known as cutheparine), and low molecular weight heparin (also known as ardeparin sodium). Other examples include heparan sulfate, heparinoids, heparin-based compounds and heparin having a hydrophobic counter-ion.

Examples of other polysaccharides include glycosaminoglycans (or mucopolysaccharides) such as keratan sulfate, chondroitin sulfate, dermatan sulfate (also known as β-heparin or as chondroitin sulfate B), hyaluronic acid and hyaluronates.

According to another aspect of the present invention, the reservoir layer 3 can comprise highly positively charged peptides or proteins, such as L-arginine or oligomers and polymers of L-arginine. These oligomers and polymers are oligo- or polycationic peptides (or proteins) and are products of self-polycondensation of an amino acid L-arginine, also known as 2-amino-5-guanidinovaleric acid having a formula $$NH=C(NH_2)-NH-CH_2-CH_2-CH_2-CH(NH_2)-COOH.$$

One example of oligomeric L-arginine that can be used is a heptamer known as R7. Oligomers and polymers of L-arginine can be used in a form of a derivative, such as a salt, for example, hydrochloride, trifluoroacetate, acetate, or sulfate salts. Oligomers and polymers of L-arginine, including R7, for the purposes of the present invention are collectively designated as PArg. A general formula of PArg as a hydrochloride salt can be represented as H[—NH—CHR—CO—]$_m$OH.HCl, or PArg.HCl, where "m" can be an integer within a range of between 5 and 1,000 and "R" is 1-guanidinopropyl radical having the structure —CH$_2$—CH$_2$—CH$_2$—NH—C(NH$_2$)=NH. In case of R7, m equals 7. "L-arginine," "oligomers and polymers of L-arginine," or "PArg" is intended to include pure L-arginine in its monomeric, oligomeric or polymeric form as well as derivatives of L-arginine.

Formamide (H—CO—NH$_2$) can be used as a solubilizing agent for heparin, heparin derivatives, or PArg. Heparin or a heparin derivative or PArg can be dissolved in formamide. At least 8% by mass of a solution of heparin or a derivative thereof or PArg in formamide can be prepared.

A heparin-formamide solution or a PArg-formamide solution can be mixed with a polymer. Should the polymer not be capable of dissolving in formamide, the polymer can be first admixed with an organic solvent or a mixture of organic solvents capable of dissolving the polymer. The solution can be applied onto the surface of the stent or onto the primer layer 2 by spraying or dipping techniques as is well known to one of ordinary skilled in the art. Alternatively, the heparin-formamide solution or the PArg-formamide solution can be applied followed by applying the solution of the polymer in the organic solvent or the mixture of organic solvents. The process can be repeated to obtain a suitable weight of the compound on the stent.

Figure 2:
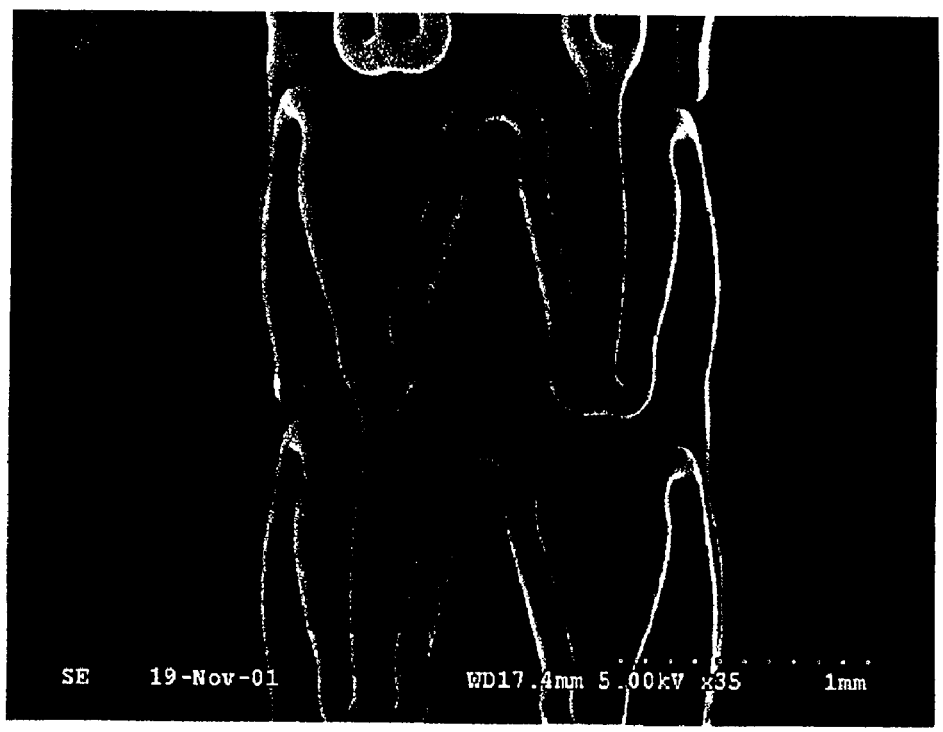
FIG. 2 is a scanning electronic micrograph (SEM) showing a coated stent, where the stent coating included heparin applied in accordance with one embodiment of the present invention.

FIG. 2 is a SEM of a stent coating which includes heparin applied according to one embodiment of the present invention. The coating shown on FIG. 2 was comprised of:

(a) a reservoir 3 having about 740 µg of total solids which included poly(ethylene-co-vinyl alcohol) (EVAL) and heparin in a 2:1 mass ratio; and (b) a topcoat layer (about 54 µg of EVAL).

As evidenced by the micrograph, a very smooth coating was obtained.

The above-mentioned poly(ethylene-co-vinyl alcohol) (EVAL) is one example of a suitable polymer than can be employed to prepare the drug-polymer layer 3, the optional primer layer 2 and/or the optional topcoat layer 4. EVAL has the general formula . EVAL is a product of hydrolysis of ethylene-vinyl acetate copolymers. EVAL can also be a terpolymer including up to, for example, 5 molar % of units derived from styrene, propylene and other suitable unsaturated monomers. Other suitable polymers that can be used include poly (hydroxyvalerate), poly(L-lactic acid), polycaprolactone, poly(lactide-co-glycolide), poly(hydroxybutyrate), poly (hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, such as poly(alkyl)(meth)acrylates, for example, poly(butyl methacrylate) and copolymers of butyl methacrylate, for instance, with hydroxymethyl methacrylate; vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose and its derivatives, cellulose acetate, cellulose butyrate, cellulose acetate butyrate, cellophane, cellulose nitrate, cellulose propionate, cellulose ethers, soluble fluorinated polymers and carboxymethyl cellulose.

The topcoat layer 4 may also contain a small amount of Na-heparin and/or PArg. The reservoir layer 3 can optionally include a therapeutic agent with or without heparin or PArg. If such an agent is to be used, the agent can be either incorporated into the heparin or PArg composition, the polymer composition, or added subsequent to the combination of these compositions. Examples such of suitable therapeutic agents include actinomycin D or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflamatory, antiplatelet, anticoagulant, antifibrin, antithrombin, antimitotic, antibiotic, antiallergic and antioxidant substances. Examples of such antineoplastics and/or antimitotics include paclitaxel (e.g. Taxol® by Bristol-Myers Squibb Co. of Stamford, Conn.), docetaxel (e.g. Taxotere®, from Aventis S.A. of Frankfurt, Germany) methotrexate, azathioprine, vincristine, vinblastine, fluorouracil, doxorubicin hydrochloride (e.g. Adriamycin® from Pharmacia & Upjohn, of Peapack N.J.), and mitomycin (e.g. Mutamycin® from Bristol-Myers Squibb Co. of Stamford). Examples of such antiplatelets, anticoagulants, antifibrin, and antithrombins include hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax® made by Biogen, Inc., of Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co. of Stamford), cilazapril or lisinopril (e.g. Prinivil® and Prinzide® from Merck & Co., Inc. of Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., of Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and its derivatives, estradiol and its derivatives, poly(ethylene glycol)/poly(ethylene oxide) and dexamethasone.

The embodiments of the present invention are described with reference to a stent, such as a self-expandable or a balloon expandable stent. Other suitable implantable medical device can also be similarly coated. Examples of such implantable devices include, but are not limited to, stent-grafts, grafts (e.g., aortic grafts), artificial heart valves, cerebrospinal fluid shunts, pacemaker electrodes, and endocardial leads (e.g., FINELINE and ENDOTAK, available from Guidant Corp.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Embodiments of the present invention are further illustrated by the following examples:

EXAMPLE 1

About 1 milliliter (1.133 gram) of formamide was added to 0.1 gram of sodium heparin (NaHep) obtained from Aldrich Chemical Co. of Milwaukee, Wis. The suspension was heated at a temperature about 70° C. After about 5 minutes of heating, sodium heparin was fully dissolved in formamide to form about 8.1 mass % NaHep solution. About 0.15 gram of EVAL was dissolved in about 0.85 gram of dimethylacetamide (DMAC) to form 15% (mass) solution of EVAL. About 1 gram of the 15% EVAL solution was further dissolved in a mixture of about 2 grams of DMAC and about 1 gram of methyl alcohol. This final EVAL solution was added to the NaHep-formamide solution prepared above. The two solutions were thoroughly mixed to form a clear heparin-polymer (NaHep-EVAL) solution. The NaHep-EVAL solution had a solid content of about 4.8 mass % and the mass ratio of NaHep to EVAL of about 2:3.

At room temperature, the NaHep-EVAL solution was not sufficiently stable and developed substantial turbidity within about 15 minutes after the mixing of the NaHep: formamide solution and the EVAL solution. In order to avoid the phase separation, the NaHep-EVAL solution was heated at about 70° C. for several minutes until the solution had become clear again. When kept at a temperature of about 40° C., the NaHep-EVAL solution was clear and stable.

Prior to application, the NaHep-EVAL solution was filtered through 0.45 micron filter. The NaHep-EVAL solution was then applied to a stent using a spray apparatus, such as an EFD 780S spray nozzle with a VALVEMATE 7040 control system, manufactured by EFD, Inc. of East Providence, R.I. The EFD 780S spray nozzle is an air-assisted external mixing atomizer. The composition was atomized by air and applied to the stent surfaces at a pressure of about 103.4 kPa (15 psi or 1.03 atm). The distance between the spray nozzle and the stent surface was about 105 mm. The NaHep-EVAL solution was fed to the spray block at a pressure of about 23.3 kPa (3.35 psi or 0.23 atm).

The container with NaHep-EVAL solution was maintained at a temperature of about 40° C., in order to avoid possible precipitation of the polymer or the drug. The spray block temperature was kept at about 60° C. During the process of applying the composition, the stent can be optionally rotated about its longitudinal axis, at a speed of 50 to about 150 rpm. The stent can also be linearly moved along the same axis during the application.

The NaHep-EVAL solution was applied to a 18-mm TETRA stent (available from Guidant Corp.) in a series of 10-second passes, to deposit about 45 µg of coating per spray pass. Between the spray passes, the stent was dried for 10 seconds using flowing air with a temperature of about 80° C. to 100° C. A total of about 1.2 milligram of solid mass was applied. The coated stent was partially dried overnight at room temperature. Upon visual inspection, no pool webs were observed.

EXAMPLE 2

About 1 milliliter (1.133 gram) of formamide was added to about 0.1 gram of poly-L-arginine sulfate. The suspension was heated at a temperature of 50° C. After a few minutes of heating, PArg was fully dissolved in formamide to form about 8.1 mass % PArg solution. About 0.15 gram of EVAL was dissolved in about 0.85 gram of DMAC to form 15% (mass) solution of EVAL. About 1 gram of the 15% EVAL solution was further dissolved in a mixture of about 2 grains of DMAC and about 1 gram of methyl alcohol. This final EVAL solution was added to the PArg-formamide solution. The two solutions were thoroughly mixed to form the PArg-EVAL solution. The PArg-EVAL solution had a solid content of about 4.8 mass % and the mass ratio of PArg to EVAL of about 2:3.

At room temperature, the PArg-EVAL solution was not sufficiently stable and developed substantial turbidity within about 15 minutes after the mixing of the PArg-formamide solution with the EVAL solution. In order to avoid phase separation, the PArg-EVAL solution was heated at about 70° C. for several minutes until the solution became clear again. When kept at a temperature of about 40° C., the PArg-EVAL solution was clear and stable.

Using the process and equipment described in Example 1, the PArg-EVAL solution was applied to an 8-mm TETRA stent. 10 μg of coating per spray pass was applied. Between the spray passes, the stent was dried for 10 seconds using flowing air with a temperature of about 80° C. to 100° C. A total of about 500 milligram of solid mass was applied. Upon visual inspection, no pool webs were observed.

EXAMPLE 3

A drug-polymer layer containing NaHep-EVAL was formed on a stent according to the procedure described in Example 1. A 2% (mass) solution of EVAL in DMAC was prepared by mixing about 2 grams of EVAL and about 98 grams of DMAC. Using the process and equipment described in Example 1, the 2% EVAL solution was applied to an 8-mm TETRA stent coated with the NaHep-EVAL drug-polymer layer to form a topcoat layer. About 10 μg of & coating per spray pass was deposited. A total of about 33 μg of solid mass was applied as a topcoat layer followed by drying in a convection oven at about 70° C. for about 2 hours.

Using the process and equipment described in Example 1, the 2% EVAL solution was also applied to an 18-mm TETRA stent coated with the NaHep-EVAL drug-polymer layer to form a topcoat layer. About 20 μg of coating per spray pass was deposited. A total of about 120 μg of solid mass was applied as a topcoat layer followed by drying in a convection oven at about 70° C. for about 2 hours.

EXAMPLE 4

A drug-polymer layer containing PArg-EVAL was formed on a stent according to the procedure described in Example 1. A 2% (mass) solution of EVAL in DMAC was prepared by mixing about 2 grams of EVAL and about 98 grams of DMAC. Using the process and equipment described in Example 1, the 2% EVAL solution was applied on an 8-mm TETRA stent coated with the PArg-EVAL drug-polymer layer to form a topcoat layer. About 10 μg of coating per spray pass was deposited. A total of about 40 μg of solid mass was applied as a topcoat layer followed by drying in a convection oven at about 70° C. for about 2 hours.

Using the process and equipment described in Example 1, the 2% EVAL solution was also applied to an 18-mm TETRA stent coated with the PArg-EVAL drug-polymer layer to form a topcoat layer. About 20 μg of coating per spray pass was deposited. A total of about 400 μg of solid mass was applied as a topcoat followed by drying in a convection oven at about 70° C. for about 2 hours.

While particular embodiments of the present invention have been shown and described, it 1 g will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A therapeutic composition comprising a polysaccharide or a cationic peptide dissolved in an organic substance comprising formamide.

2. The composition of claim 1, wherein the polysaccharide is selected from a group consisting of heparin, heparin salts, heparinoids, heparin-based compounds, heparin having a hydrophobic counter-ion, dermatan sulfate, keratan sulfate, chondroitin sulfate, hyaluronic acid and hyaluronates.

3. A therapeutic composition comprising a polysaccharide or a cationic peptide dissolved in an organic substance, wherein the cationic peptide comprises oligo-L-arginine or poly-L-arginine.

4. The composition of claim 3, wherein the organic substance comprises formamide.

5. A method of coating an implantable medical device, comprising applying the composition of claim 1 to the device and removing the organic substance.

6. A therapeutic composition comprising (a) a polysaccharide or a cationic peptide or protein; (b) formamide; and optionally (c) one or a combination of any of a polymer, a therapeutic substance and a solvent for the polymer and/or the therapeutic substance.

7. The therapeutic composition of claim 6, wherein the polysaccharide is heparin.

8. The therapeutic composition of claim 6, wherein the polysaccharide comprises an alkali metal salt of heparin.

9. The therapeutic composition of claim 6, wherein the polysaccharide comprises an alkaline-earth metal salt of heparin.

10. The therapeutic composition of claim 6, wherein the polysaccharide comprises a sodium heparin.

11. The therapeutic composition of claim 6, wherein the polysaccharide comprises a potassium heparin.

12. The therapeutic composition of claim 6, wherein the polysaccharide comprises a lithium heparin.

13. The therapeutic composition of claim 6, wherein the polysaccharide comprises a calcium heparin.

14. The therapeutic composition of claim 6, wherein the polysaccharide comprises a magnesium heparin.

15. The therapeutic composition of claim 6, wherein the polysaccharide comprises a low molecular weight heparin.

16. The therapeutic composition of claim 6, wherein the polysaccharide comprises a heparin sulfate.

17. The therapeutic composition of claim 6, wherein the polysaccharide comprises a heparinoid.

18. The therapeutic composition of claim 6, wherein the polysaccharide comprises heparin having a hydrophobic counter-ion.

19. The therapeutic composition of claim 6, wherein the polysaccharide comprises a glycosaminoglycan.

20. The therapeutic composition of claim 6, wherein the polysaccharide comprises keratan sulfate.

21. The therapeutic composition of claim 6, wherein the polysaccharide comprises chondroitin sulfate.

22. The therapeutic composition of claim 6, wherein the polysaccharide comprises dermatan sulfate.

23. The therapeutic composition of claim 6, wherein the polysaccharide comprises hyaluronic acid.

24. The therapeutic composition of claim 6, wherein the polysaccharide comprises a hyaluronate.

25. The therapeutic composition of claim 6, wherein the cationic peptide comprises oligomers or polymers of L-argenine, or derivatives or salts thereof.

26. The therapeutic composition of claim 6, wherein the cationic peptide comprises R7.

27. The therapeutic composition of claim 6, wherein the therapeutic substance is paclitaxel, decetaxel, rapamycin, or derivatives thereof.

28. The therapeutic composition of claim 1, wherein the polysaccharide is heparin.

29. The therapeutic composition of claim 1, wherein the polysaccharide comprises an alkali metal salt of heparin.

30. The therapeutic composition of claim 1, wherein the polysaccharide comprises an alkaline-earth metal salt of heparin.

31. The therapeutic composition of claim 1, wherein the polysaccharide comprises a sodium heparin.

32. The therapeutic composition of claim 1, wherein the polysaccharide comprises a potassium heparin.

33. The therapeutic composition of claim 1, wherein the polysaccharide comprises a lithium heparin.

34. The therapeutic composition of claim 1, wherein the polysaccharide comprises a calcium heparin.

35. The therapeutic composition of claim 1, wherein the polysaccharide comprises a magnesium heparin.

36. The therapeutic composition of claim 1, wherein the polysaccharide comprises a low molecular weight heparin.

37. The therapeutic composition of claim 1, wherein the polysaccharide comprises a heparin sulfate.

38. The therapeutic composition of claim 1, wherein the polysaccharide comprises a heparinoid.

39. The therapeutic composition of claim 1, wherein the polysaccharide comprises heparin having a hydrophobic counter-ion.

40. The therapeutic composition of claim 1, wherein the polysaccharide comprises a glycosaminoglycan.

41. The therapeutic composition of claim 1, wherein the polysaccharide comprises keratan sulfate.

42. The therapeutic composition of claim 1, wherein the polysaccharide comprises chondroitin sulfate.

43. The therapeutic composition of claim 1, wherein the polysaccharide comprises dermatan sulfate.

44. The therapeutic composition of claim 1, wherein the polysaccharide comprises hyaluronic acid.

45. The therapeutic composition of claim 1, wherein the polysaccharide comprises a hyaluronate.

46. The therapeutic composition of claim 1, wherein the cationic peptide comprises oligomers or polymers of L-argenine, or derivatives or salts thereof.

47. The therapeutic composition of claim 1, wherein the cationic peptide comprises R7.

48. The therapeutic composition of claim 1, additionally included a polymer.

49. The therapeutic composition of claim 1, additionally including a therapeutic substance.

50. The therapeutic composition of claim 1, additionally including paclitaxel, docetaxel, rapamycin, or derivatives thereof.

51. A therapeutic composition comprising heparin dissolved in an organic solvent, wherein the organic solvent comprises formamide.

52. The therapeutic composition of claim 51, wherein dissolved is defined as at least 8% mass of heparin solubility in the organic solvent.

53. The therapeutic composition of claim 51, additionally including one or a combination of a polymer, a therapeutic substance and a solvent.

54. A method of coating an implantable medical device, comprising applying the composition of claim 6 to the device and removing the formamide and if applicable the solvent.

55. A method of coating an implantable medical device, comprising applying the composition of claim 51 to the device and removing the organic solvent.

56. The method of claim 55, wherein the composition additionally comprises one or a combination a polymer, a therapeutic substance and a solvent.

57. The method of claim 56, wherein the therapeutic substance is paclitaxel, decetaxel, rapamycin, or derivatives thereof.

58. The method of claim 55, wherein the device is a stent.

59. The method of claim 54, wherein the device is a stent.

60. The method of claim 54, wherein the therapeutic substance if used is paclitaxel, decetaxel, rapamycin, or derivatives thereof.

61. The method of claim 5, wherein the device is a stent.

* * * * *